(12) United States Patent
Graf et al.

(10) Patent No.: US 6,336,940 B1
(45) Date of Patent: Jan. 8, 2002

(54) GRAFT ANCHOR

(75) Inventors: Ben K. Graf, Madison, WI (US); Michael C. Ferragamo, North Dighton, MA (US); Rebecca A. Blough, Warwick, RI (US); Charles H. Brown, Jr., Wellesley, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/541,172

(22) Filed: Apr. 3, 2000

Related U.S. Application Data

(62) Division of application No. 08/800,961, filed on Feb. 18, 1997, now Pat. No. 6,231,606, which is a continuation of application No. 08/602,706, filed on Feb. 16, 1996, now abandoned.

(51) Int. Cl.$^7$ .................................................. A61F 2/08
(52) U.S. Cl. ..................................... 623/13.14; 128/898
(58) Field of Search ....................... 623/13.14; 606/232, 606/72, 73; 128/898

(56) References Cited

U.S. PATENT DOCUMENTS

| | | | |
|---|---|---|---|
| 4,013,071 A | 3/1977 | Rosenberg | 128/92 |
| 4,246,660 A | * 1/1981 | Wevers | 3/1 |
| 4,259,072 A | 3/1981 | Hirabayashi et al. | 433/173 |
| 4,590,928 A | 5/1986 | Hunt et al. | 128/92 |
| 4,632,100 A | 12/1986 | Somer et al. | 128/92 |

(List continued on next page.)

FOREIGN PATENT DOCUMENTS

| | | |
|---|---|---|
| DE | 196 49 450 A1 | 6/1998 |
| EP | 0 279 129 B1 | 3/1991 |
| FR | 2 590 792 | 5/1987 |
| GB | 2 248 778 A | 4/1992 |
| GB | 2 288 739 A | 11/1995 |

OTHER PUBLICATIONS

Robertson et al., "Soft Tissue Fixation to Bone", The American Journal of Sports Medicine, vol. 14, No. 5, 1986.

Brown et al., "Anterior Cruciate Ligament Injuries", Traumatic Disorders of the Knee, Chapter 14, pp. 215–218, 238–254, 277–284.

Otero, M.D., et al., "A Comparison of th edoubled Semitendinosus/Gracilis and Central Third of the Patellar Tendon Autografts . . . ", The Journal of Arthroscopic and Related Surgery, 9(2):143–148.

Rosenberg, M.D., et al., Techniques for ACL Reconstruction with Mulit–Trac Drill Guide, Acufex Microsurgical, Inc., 1994.

"Washerloc Tibial Fixation Device for Soft Tissue Grafts", Arthotek, Inc., 1997.

Howell, "Why the Double–Looped Semitendinosus and Gracilis Graft . . . ", pp. 1–9.

Innovasive Devices, Inc., "GeoFit Screw & Washer System", 1997.

* cited by examiner

Primary Examiner—Corrine McDermott
Assistant Examiner—Thomas C. Barrett
(74) Attorney, Agent, or Firm—Fish & Richardson PC

(57) ABSTRACT

A graft anchor includes an anchor member for placement in bone tissue. The anchor member defines an opening. An inner member is insertably securable into the anchor member opening. A fastener is configured such that insertion and securing of the inner member into the anchor member opening results in a holding force being applied to the graft. The anchor member is of limited length to maintain its distal end within the bone. The anchor member includes a distal drive opening for receiving a drive tool and the inner member includes a proximal drive opening for receiving the drive tool. The fastener includes channels for containing the graft, a fastener body with protrusions extending from the fastener body for penetrating bone tissue, and a reinforcing member contained within the fastener body.

12 Claims, 8 Drawing Sheets

U.S. PATENT DOCUMENTS

| | | | | |
|---|---|---|---|---|
| 4,632,101 A | | 12/1986 | Freedland | 128/922 |
| 4,708,132 A | * | 11/1987 | Silvestrini | 128/92 |
| 4,716,893 A | | 1/1988 | Fischer et al. | 128/92 |
| 4,721,103 A | | 1/1988 | Freedland | 128/92 |
| 4,759,765 A | | 7/1988 | Van Kampen | 623/13 |
| 4,793,335 A | * | 12/1988 | Frey et al. | 128/92 |
| 4,834,752 A | * | 5/1989 | Van Kampen | 623/13 |
| 4,870,957 A | | 10/1989 | Goble et al. | 128/92 |
| 4,950,271 A | | 8/1990 | Lewis et al. | 606/102 |
| 4,960,420 A | | 10/1990 | Goble et al. | 606/72 |
| 4,988,351 A | | 1/1991 | Paulos et al. | 606/72 |
| 5,013,316 A | | 5/1991 | Goble et al. | 606/72 |
| 5,108,431 A | | 4/1992 | Mansat et al. | 623/13 |
| 5,139,499 A | | 8/1992 | Small et al. | 606/73 |
| 5,139,520 A | | 8/1992 | Rosenberg | 623/13 |
| 5,152,790 A | | 10/1992 | Rosenberg et al. | 623/13 |
| 5,167,665 A | | 12/1992 | McKinney | 606/75 |
| 5,176,682 A | | 1/1993 | Chow | 606/72 |
| 5,209,756 A | | 5/1993 | Seedhom et al. | 606/151 |
| 5,269,784 A | | 12/1993 | Mast | 606/69 |
| 5,306,301 A | | 4/1994 | Graf et al. | 623/13 |
| 5,314,427 A | | 5/1994 | Goble et al. | 606/72 |
| 5,352,229 A | | 10/1994 | Goble et al. | 606/72 |
| 5,364,400 A | | 11/1994 | Rego, Jr. et al. | 606/72 |
| 5,374,269 A | | 12/1994 | Rosenberg | 606/80 |
| 5,376,119 A | | 12/1994 | Zimmermann et al. | 673/13 |
| 5,380,334 A | | 1/1995 | Torrie et al. | 606/104 |
| 5,423,819 A | | 6/1995 | Small et al. | 606/73 |
| 5,425,767 A | | 6/1995 | Steininger et al. | 623/13 |
| 5,501,695 A | | 3/1996 | Anspach, Jr. et al. | 606/232 |
| D368,777 S | * | 4/1996 | Goble et al. | D24/145 |
| 5,522,843 A | | 6/1996 | Zang | 606/232 |
| 5,545,165 A | | 8/1996 | Biederman et al. | 606/61 |
| D374,286 S | * | 10/1996 | Goble et al. | D24/145 |
| D374,482 S | * | 10/1996 | Goble et al. | D24/145 |
| D375,791 S | * | 11/1996 | Goble et al. | D24/145 |
| 5,571,184 A | | 11/1996 | DeSatnick | 623/13 |
| 5,718,706 A | | 2/1998 | Roger | 606/73 |

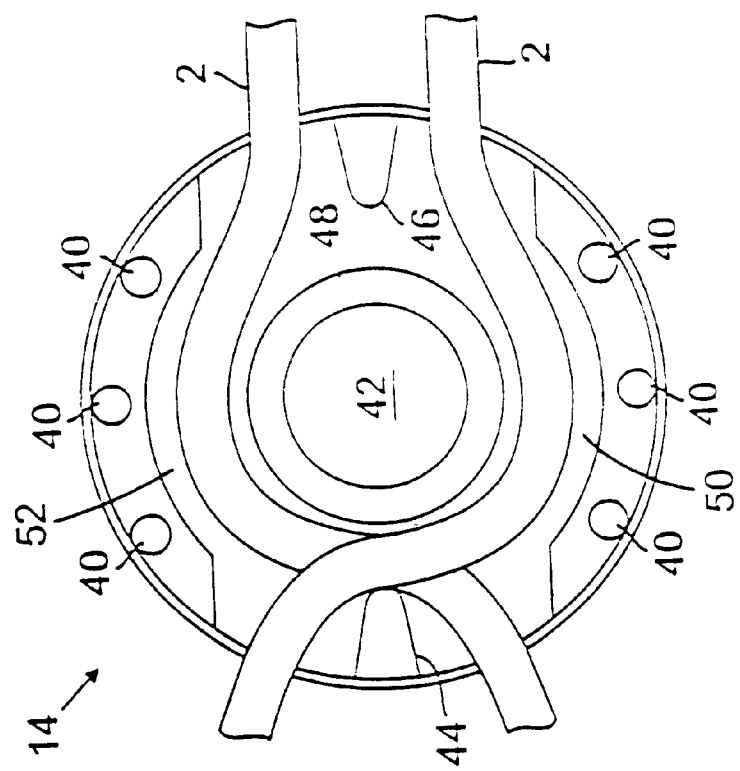
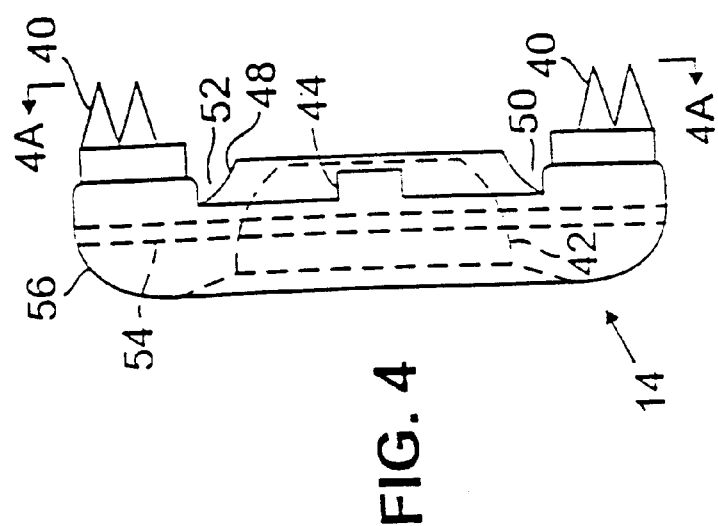

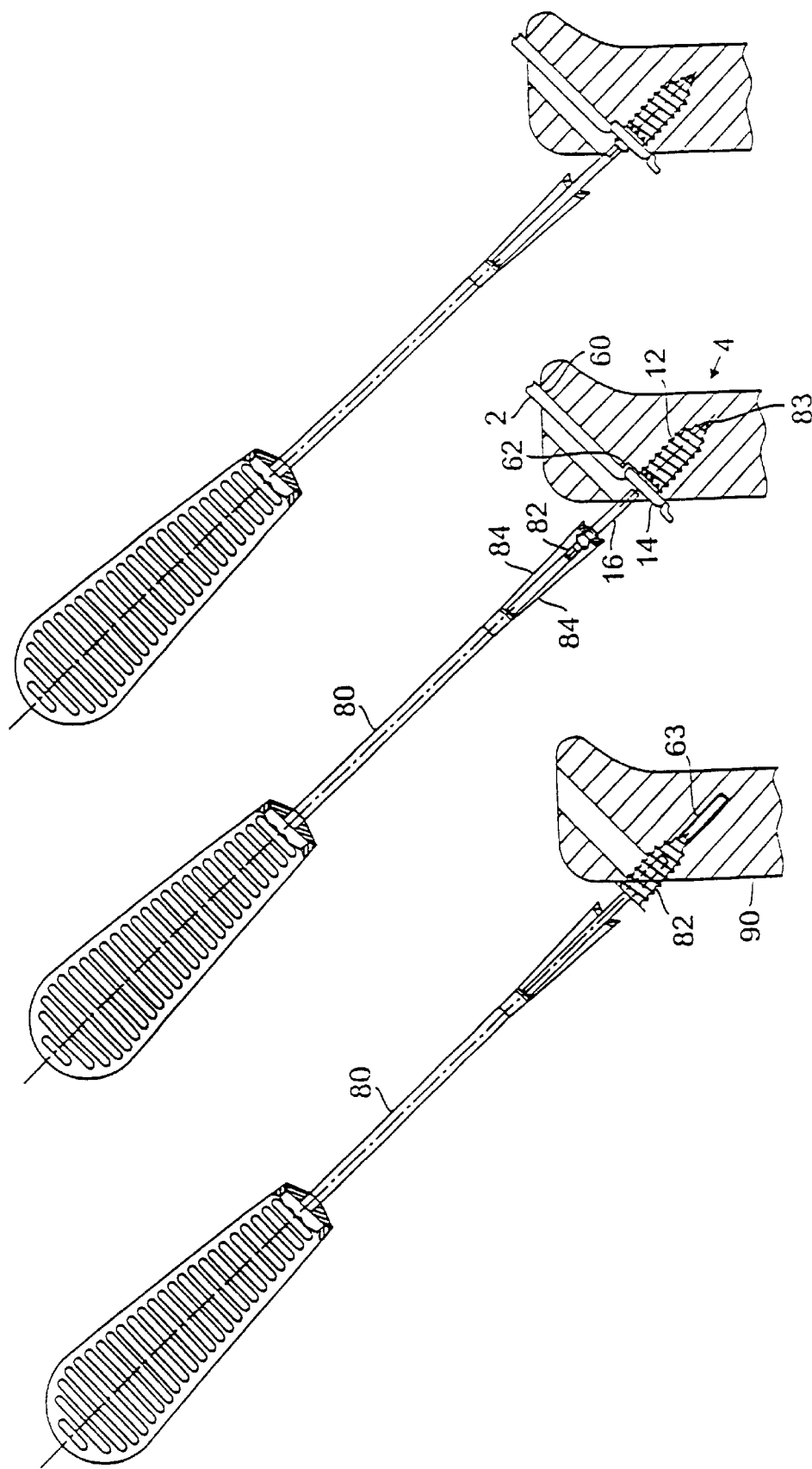

GRAFT ANCHOR

CROSS-REFERENCE TO RELATED APPLICATION

This application is a divisional of U.S. Pat. No. 6,231,606, filed Feb. 18, 1997, which is a continuation of application Ser. No. 08/602,706, filed Feb. 16, 1996, now abandoned.

BACKGROUND OF THE INVENTION

The invention relates to an apparatus and method for securing a graft to bone.

Reconstruction of the anterior cruciate ligament (ACL) generally involves the placement of a tendon graft through a tibial tunnel and securing the graft at one end to the femur and at the other end to the tibia. It is known to secure the graft to the tibia using staples, a bicortical screw and a fastening washer having spikes for penetration into the bone, or a suture attached to a fixation post embedded into the bone.

SUMMARY OF THE INVENTION

A graft anchor for securing a graft to bone includes an anchor member for placement in bone tissue. The anchor member defines an opening. An inner member is insertably securable into the anchor member opening. A fastener is configured such that insertion and securing of the inner member into the anchor member opening results in a holding force being applied to the graft.

In particular embodiments of the invention, the anchor member is of limited length to maintain its distal end within the bone and the opening is a threaded axial bore. The inner member includes external threads for mating with the axial bore threads and a smooth shank proximal of the external threads. The anchor member includes external, threads; the threads are preferably self-tapping. The axial bore of the anchor member includes a distal drive opening for receiving a drive tool, and the inner member includes a proximal drive opening for receiving a drive tool. The distal and proximal drive openings are preferably hexagonally shaped. The fastener includes a channel for containing the graft, a guide defining the channel, a fastener body with protrusions extending from the fastener body for penetrating bone tissue, and a reinforcing member contained within the fastener body. The fastener body has a strength less than the reinforcing member. The fastener includes a through bore and a lip surrounding the through bore which separates the graft from the through bore. The fastener body has a generally circular shape which may include two flat sides.

According to another aspect of the invention, a method of securing a graft to bone includes the steps of placing an anchor member into the bone, positioning a fastener such that a portion of the graft lies between the fastener and the bone, inserting and securing an inner member into the anchor member, the insertion forcing the fastener into the bone to secure the graft by squeezing the graft between the fastener and the bone.

In particular embodiments of the invention, the method includes drilling a counterbore in the tunnel perpendicular to a central axis of the tunnel, and drilling a hole perpendicular to the central axis of the tunnel and centered within the counterbore. Placement of the anchor member into the bone is by screwing the anchor member into the hole. The anchor member is self-tapped into the hole. The anchor member is of limited length such that placement of the anchor member into the bone results in a distal end of the anchor member being maintained within the bone. The portion of the graft that lies between the fastener and the bone is contained within a protective channel defined by the fastener.

Advantages of the invention include the low profile presented by the graft anchor because of its placement in a counterbore. The placement of the graft anchor within a counterbore creates a tortuous path for the graft to follow which produces stronger initial fixation of the graft to the bone because of the increased surface area between the graft and the bone. The placement of the graft anchor within the bone tunnel eliminates any protrusion of the graft anchor from the surface of the bone. The fastener lip shields the graft from possible damage from the act of inserting the screw into the anchor member. The smooth shank of the inner member does not cut the graft. The containment of the graft substantially within the fastener channels causes the graft to lie flat against the bone increasing the area of contact between the graft and the bone which increases the ability of the graft to heal back to the bone. The anchor member has a larger outer diameter than conventional bone anchors which increases the pull out strength of the graft anchor.

BRIEF DESCRIPTION OF THE DRAWINGS

Other objects, features and advantages of the invention will be apparent from the following description taken together with the drawings in which:

FIG. 4 is a side view of a fastener of the graft anchor;

FIG. 4A is an end view of the fastener of FIG. 4, taken along lines 4A—4A, showing the graft in place against the fastener;

DESCRIPTION OF THE PREFERRED EMBODIMENTS

Figure 1:
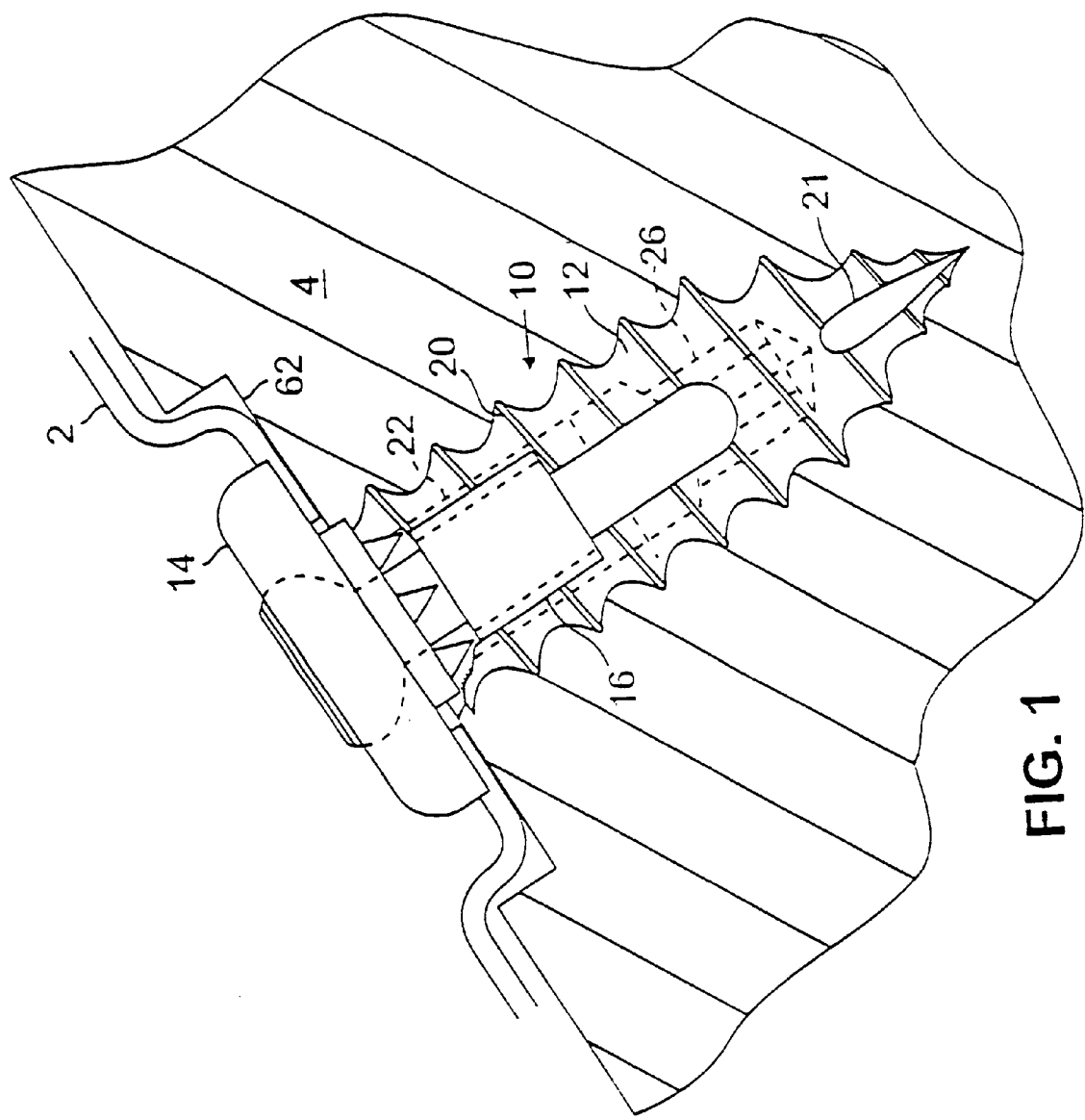
FIG. 1 shows a graft anchor according to the invention securing a graft to bone.
Figure 2A:
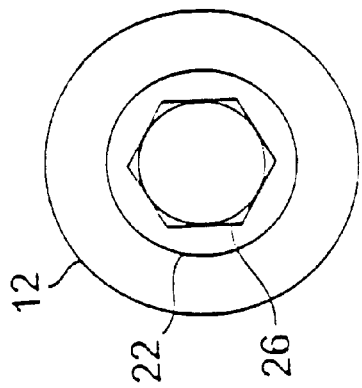
FIG. 2A is an end view of the anchor member of FIG. 2, taken along lines 2A—2A.
Figure 2:
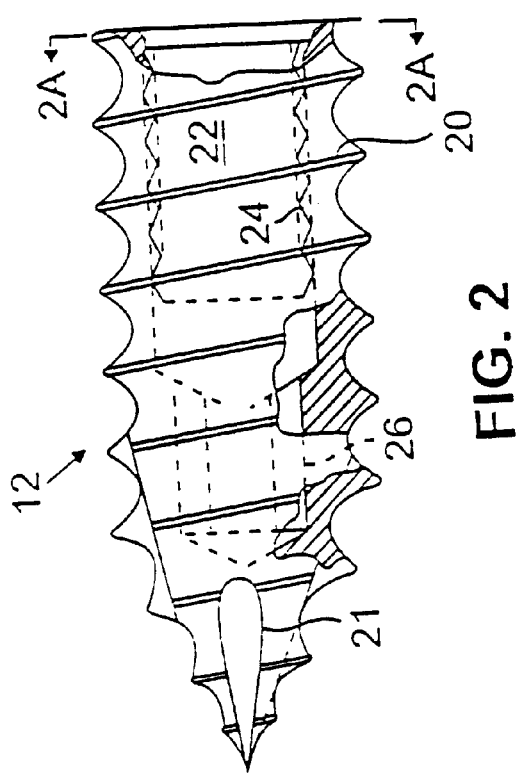
FIG. 2 is a partially cut away side view of an anchor member of the graft anchor.

Referring to FIGS. 1, 2, and 2A a graft anchor 10 for securing a graft 2 to bone 4 has an anchor member 12, a fastener 14, and a screw 16. Anchor member 12 is made from, for example, a titanium alloy, and has external threads 20 with flutes 21 to allow passage of debris during self-tapping of the anchor member, and a bore 22 having a threaded portion 24 and a distal hexagonal opening 26.

Figure 3A:
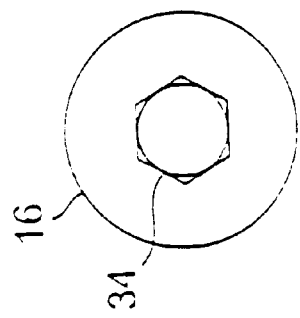
FIG. 3A is an end view of the screw of FIG. 3, taken along lines 3A—3A.
Figure 3:
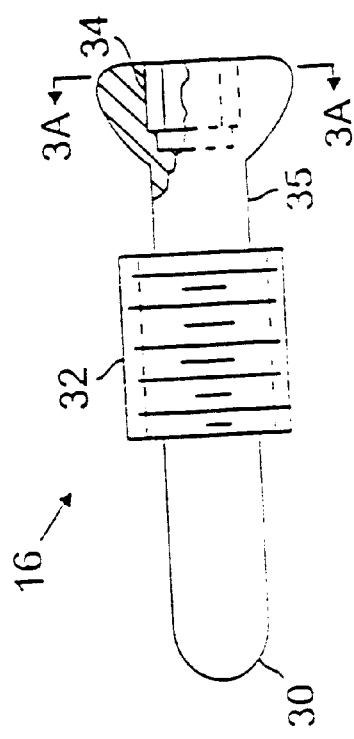
FIG. 3 is a partially cut away side view of a screw of the graft anchor.

Referring to FIGS. 3 and 3A, screw 16 is made from, for example, a titanium alloy, and includes a rounded distal end 30, a threaded portion 32 for threaded engagement with threaded portion 24 of anchor member 12, a smooth shank 35 proximal of threaded portion 32, and a proximal hexagonal opening 34.

Referring now to FIGS. 4 and 4A, fastener 14 in the illustrated embodiment of the invention, has spikes 40, a through bore 42, and guides 44 and 46 and a lip 48 which define two graft receiving channels 50 and 52. An inner strengthening ring 54 is made from, for example, a titanium alloy, while the remaining body 56 of fastener 14, which houses the strengthening ring is made from a material exhibiting less strength, for example, polyacetal, available from M. Holland Co., Northbrook, Ill.

Figure 5:
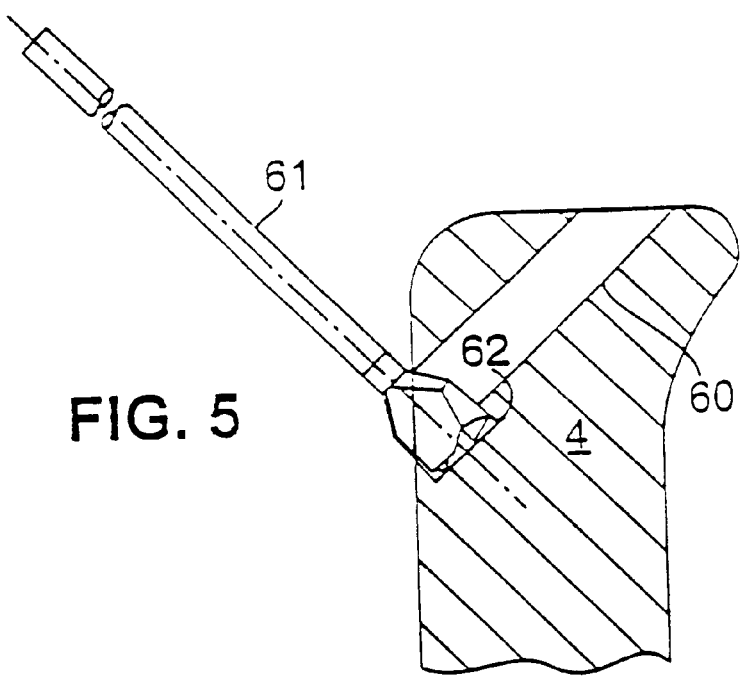
FIGS. 5–5D illustrate how the graft anchor is inserted into bone.
Figure 5A:
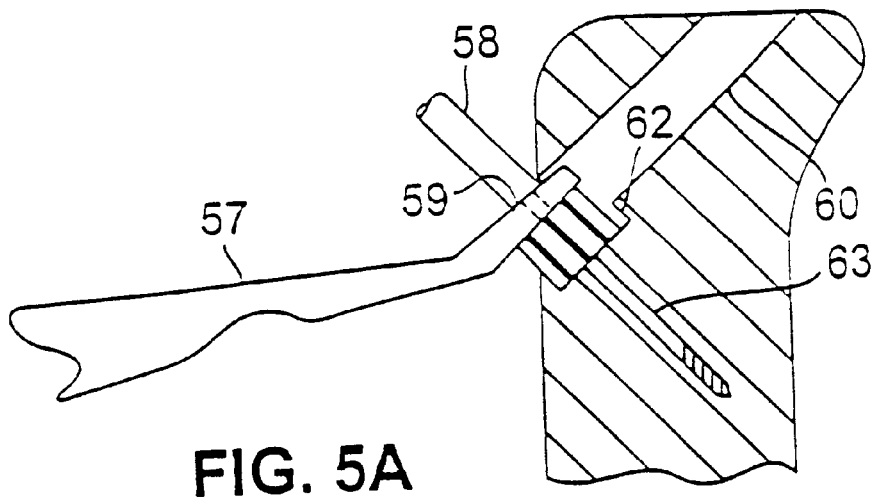

Referring to FIGS. 5–5D, in use, graft anchor 10 is preferably placed within a counterbore 62 oriented perpendicular to, for example, a 9 mm bone tunnel 60. Counterbore 62 is drilled with, for example, a 13 mm flat bottom drill 61. Referring particularly to FIG. 5A, a hole 63 is then drilled into the bone, perpendicular to bone tunnel 60, and centered within counterbore 62. A drill guide 57 and a drill 58 having a shoulder 59 are used to center hole 63 within counterbore 62 and to drill hole 63 to the desired depth. In the illustrated embodiment the desired depth of the hole is about 1.7".

Anchor member 12 is then screwed, self-tapped, into hole 63 with a drive tool 80 (FIG. 5B) having a hex end 82 that mates with hex opening 26 of anchor member 12. The anchor member is advanced into the bone until it lies flush or slightly below the surface of the bone. Though the anchor member can extend bicortically, it need not extend bicortically to provide adequate fixation. With the distal end 83 of anchor member 12 lying within cancellous bone, there is no protrusion of the graft anchor out the far side of the bone which could cause irritation. Whereas bicortical screws come in multiple sizes and the surgeon must size the screw to the particular patient, graft anchor 10 is substantially a one-size fits all system which speeds up the time of insertion. Additionally, if distal end 83 of anchor member 12 is to lie in cancellous bone, during the insertion of anchor member 12 into the bone the surgeon does not need to align the anchor member to find the far cortex.

Referring particularly to FIG. 5C, graft 2 is then fed through bone tunnel 60 and fastener 14 is placed over the graft with the graft substantially positioned in channels 50 and 52. Graft 2 is crosses within fastener 14 (see FIG. 4A) which further secures the graft within the channels. Graft 2 may partially extend under spikes 40. Hex end 82 of drive tool 80 is then positioned in hex opening 34 in screw 16 with screw 16 held by fingers 84 of drive tool 80. Screw 16 is then placed through bore 42 of fastener 14 and is advanced into threaded bore 22 of anchor member 12 by rotation of drive tool 80. The rounded distal end 30 of screw 16 aids in placement of the screw into bores 22 and 42. Lip 48 of fastener 14 separates graft 2 from screw 16 protecting the graft from possible damage resulting from being caught in the threads of the screw.

After initial engagement of the screw with anchor member 12, fingers 84 can be retracted (see FIG. 5D) to allow the screw to be further advanced. Tightening of screw 16 into anchor member 12 forces spikes 40 of fastener 14 into bone 4 and squeezes graft 2 between the fastener and the surface of the bone, thus securing the graft to the bone. Smooth shank 35 of screw 16 further protects graft 2 from damage during tightening of the screw.

Figure 7:
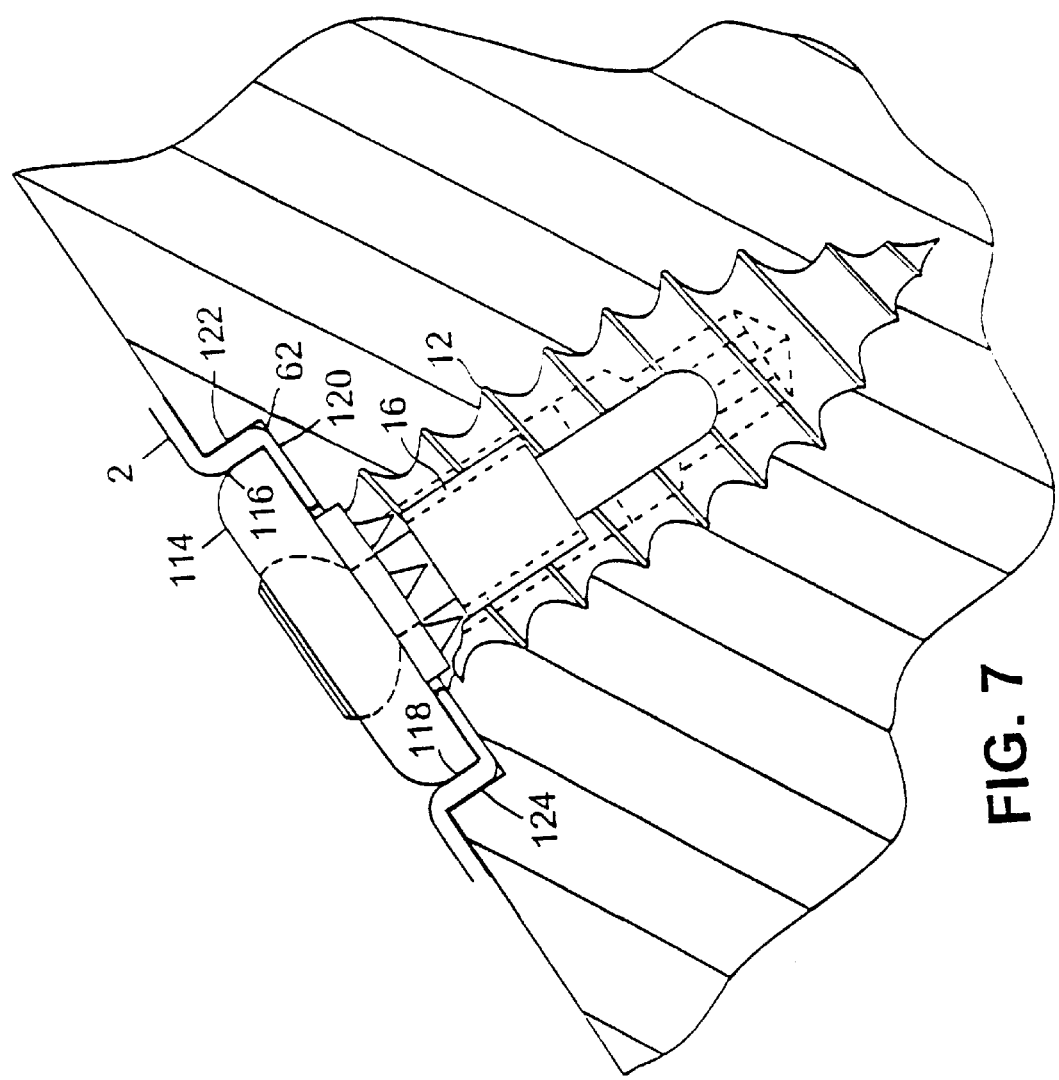
FIG. 7 shows a graft anchor including the fastener of FIG. 6 securing a graft to bone.
Figure 6:
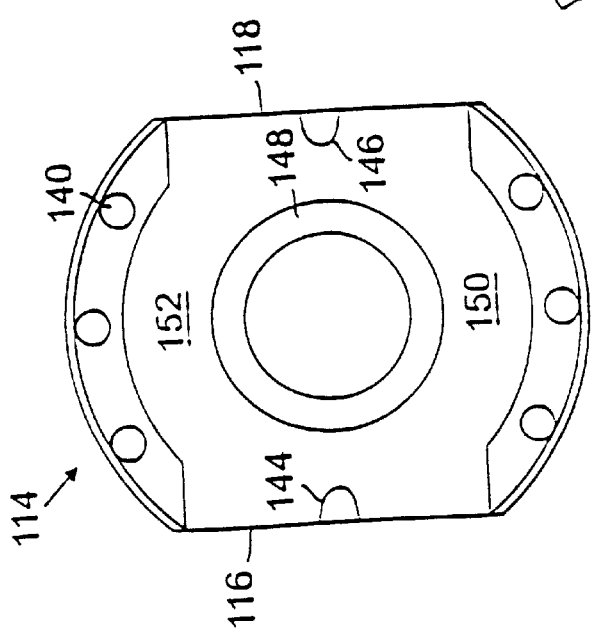
FIG. 6 is an end view of an alternative embodiment of a fastener.

Referring to FIGS. 6 and 7, to facilitate placement of a fastener within counterbore 62 located in bone tunnel 60, a preferred spiked fastener 114 including flat sides 116 and 118 can be used with anchor member 12 and screw 16. Fastener 114 includes spikes 140, guides 144 and 146, lip 148, and channels 150 and 152. The flat sides of fastener 114 aid in aligning the fastener with graft 2 and in guiding the graft into channels 50 and 52 in the area or limited access in tunnel 60. Additionally, with spiked fastener 114 placed in counterbore 62, a force, in addition to the one created by squeezing graft 2 between fastener 114 and surface 120 of counterbore 62, is applied to graft 2 by the squeezing of the graft between the flat sides 116 and 118 of the washer and the sides 122 and 124 of counterbore 62. This additional force aids in securing graft 2 to the bone.

Figure 8:
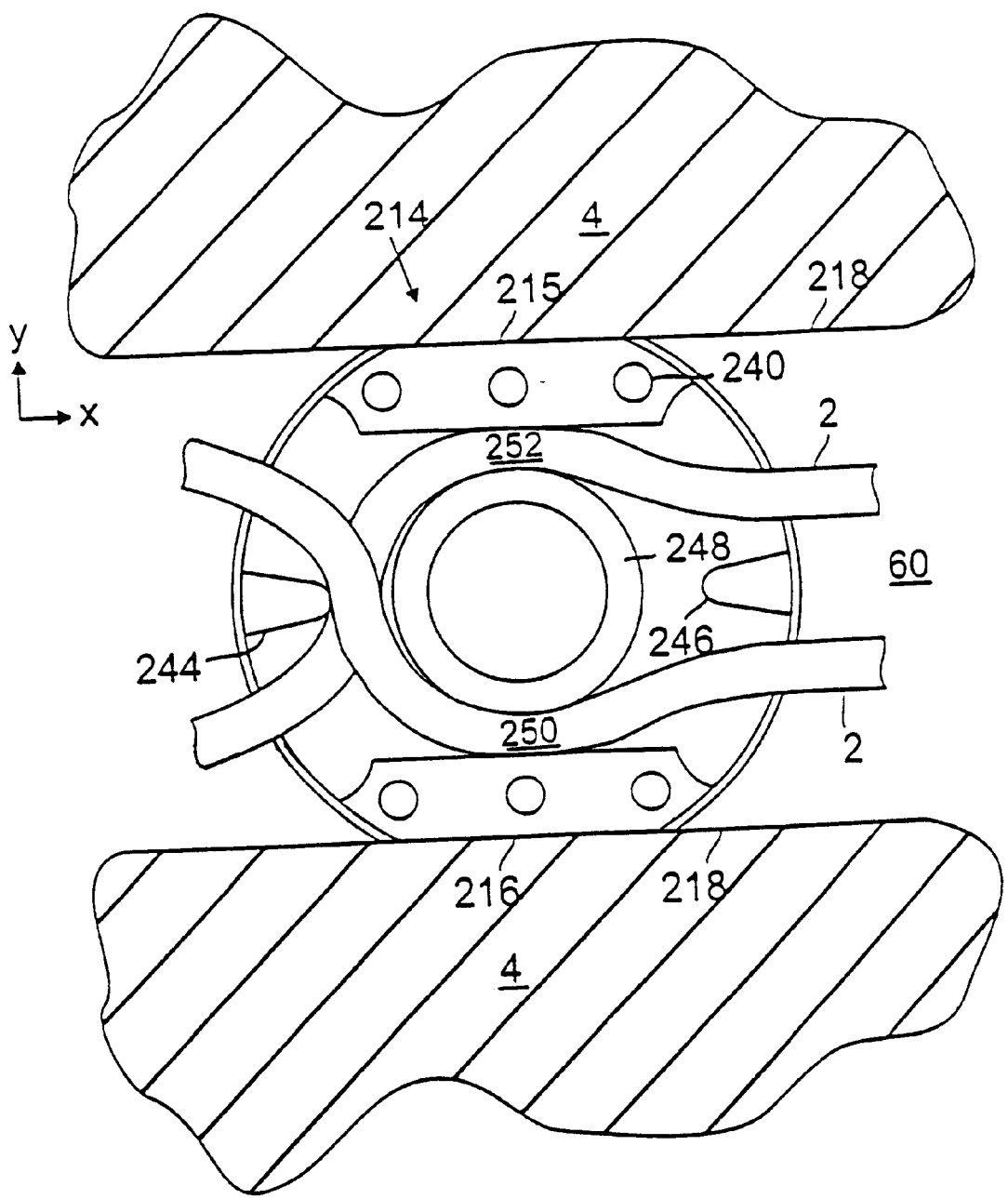
FIG. 8 is an end view of an additional alternative embodiment of a fastener.

Referring to FIG. 8, to facilitate placement of a fastener within bone tunnel 60 and particularly useful when hole 63 does not include a counterbore, a fastener 214 including flat sides 215 and 216 is are positioned within tunnel 60 such that flat sides 215 and 216 run along the direction of the walls 218 of bone tunnel 60. Fastener 214 includes spikes 240, guides 244 and 246, lip 248, and channels 250 and 252. Fastener 214, having a longer dimension along the x axis than the y axis, increases the area of contact between graft 2 and the bone as compared to a fastener having a circular profile. Flat sides 215 and 216 also align fastener 214 with the long axis of bone tunnel 60 as the fastener is placed in the bone hole which helps align graft 2 within channels 250 and 252.

Figure 9:
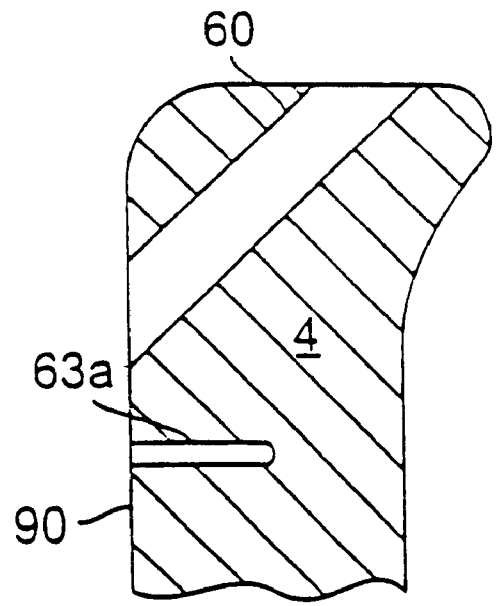
FIGS. 9 and 9A show an alternative placement of the graft anchor of FIG. 1.
Figure 9A:
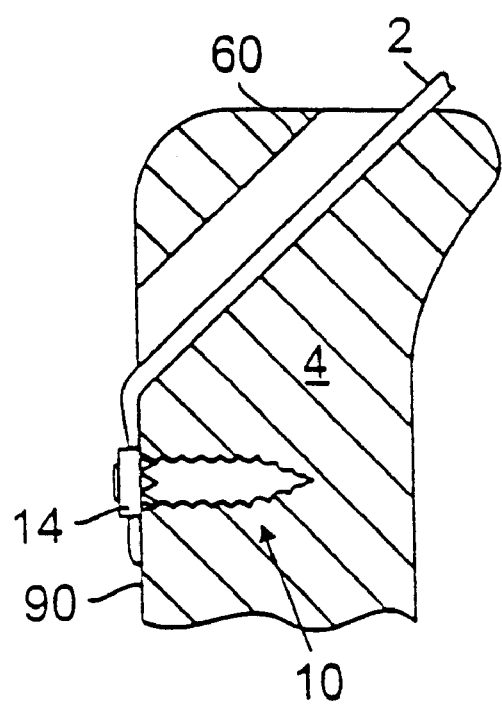

Referring to FIGS. 9 and 9A, in an alternative placement of graft anchor 10, hole 63a for placement of the graft anchor is drilled through bone surface 90. Graft anchor 10 is then used to anchor graft 2 to the bone, as described previously. In this configuration washer 14 is placed flush against bone surface 90, not within a counterbore, because drilling of a counterbore would remove additional cortical layer of the bone weakening the bone.

In addition to ACL repair, the graft anchor can be used in other soft tissue fixation applications such as medial collateral ligament (MCL) repair where the graft runs along the external surface of the bones from the tibia to the femur and may be anchored at one or both ends using graft anchor 10.

Additions, subtractions and other modifications of the illustrated embodiments of the invention will be apparent to those practiced in the art and are within the scope of the following claims.

What is claimed is:

1. A method of securing a graft to bone, comprising the steps of:

placing an anchor member into the bone, thereafter positioning a fastener such that a portion of the graft lies between the fastener and the bone, and inserting and securing an inner member into the anchor member, the insertion forcing the fastener into the bone to secure the graft by squeezing the graft between the fastener and the bone.

2. The method of claim 1 further comprising the steps of:

drilling a bone tunnel, drilling a counterbore in the tunnel perpendicular to a central axis of the tunnel, and drilling a hole perpendicular to the central axis of the tunnel and centered within the counterbore, placement of said anchor member into the bone comprises the step of screwing the anchor member into the hole.

3. The method of claim 2 wherein said anchor member is self-tapped into the hole.

4. The method of claim 1 wherein said anchor member is of limited length such that placement of said anchor member into the bone results in a distal end of the anchor member being maintained within the bone.

5. The method of claim 1 wherein the portion of the graft that lies between the fastener and the bone is contained within a protective channel defined by the fastener.

6. A method of securing a graft to bone comprising the steps of:
   drilling a bone tunnel,
   drilling a counterbore in the tunnel perpendicular to a central axis of the tunnel, drilling a hole perpendicular to the central axis of the tunnel and centered within the counterbore,
   placing an anchor member into the bone by screwing the anchor member into the hole,
   positioning a fastener such that a portion of the graft lies between the fastener and the bone, and
   inserting and securing an inner member into the anchor member, the insertion forcing the fastener into the bone to secure the graft by squeezing the graft between the fastener and the bone.

7. The method of claim 6 wherein said anchor member is self-tapped into the hole.

8. A method of securing a graft to bone comprising the steps of:
   placing an anchor member into the bone such that a proximal end of the anchor member is maintained within the bone,
   positioning a fastener such that a portion of the graft lies between the fastener and the bone, and
   inserting and securing an inner member into the anchor member, the insertion forcing the fastener into the bone to secure the graft by squeezing the graft between the fastener and the bone.

9. A method of securing a graft to bone comprising the steps of:
   placing an anchor member into the bone,
   positioning a fastener such that a portion of the graft lies between the fastener and the bone, the fastener defining a protective channel, and
   inserting and securing an inner member into the anchor member, the insertion forcing the fastener into the bone to secure the graft by squeezing the graft between the fastener and the bone with the portion of the graft at least partially retained within the protective channel.

10. The method of claim 9 further comprising providing the fastener with the protective channel substantially traversing a tissue facing surface of the fastener.

11. A method of securing a graft to bone comprising the steps of:
    screwing an anchor member into the bone,
    positioning a fastener such that a portion of the graft lies between the fastener and the bone, and
    inserting and securing an inner member into the anchor member, the insertion forcing the fastener into the bone to secure the graft by squeezing the graft between the fastener and the bone.

12. A method of securing a graft to bone comprising the steps of:
    placing an anchor member into the bone,
    positioning the graft such that a proximal end of the anchor member is distal to the graft,
    positioning a fastener such that a portion of the graft lies between the fastener and the bone, and
    inserting and securing an inner member into the anchor member, the insertion forcing the fastener into the bone to secure the graft by squeezing the graft between the fastener and the bone.

* * * * *